(12) United States Patent
Nielsen et al.

(10) Patent No.: US 10,264,983 B2
(45) Date of Patent: Apr. 23, 2019

(54) PATIENT MONITOR WITH USER-DEFINED MONITORED PARAMETERS

(71) Applicant: KONINKLIJKE PHILIPS N.V., Eindhoven (NL)

(72) Inventors: Larry Nielsen, Burlington, MA (US); Mohammed Saeed, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 835 days.

(21) Appl. No.: 14/626,064

(22) Filed: Feb. 19, 2015

(65) Prior Publication Data

US 2015/0164345 A1    Jun. 18, 2015

Related U.S. Application Data

(63) Continuation of application No. 12/094,213, filed as application No. PCT/IB2006/054016 on Oct. 30, 2006, now abandoned.

(60) Provisional application No. 60/739,744, filed on Nov. 23, 2005.

(51) Int. Cl.
| | |
|---|---|
| *A61B 5/0205* | (2006.01) |
| *A61B 5/00* | (2006.01) |
| *G06F 19/00* | (2018.01) |
| *A61B 5/0402* | (2006.01) |
| *A61B 5/145* | (2006.01) |
| *G16H 10/20* | (2018.01) |
| *A61B 5/021* | (2006.01) |
| *A61B 5/024* | (2006.01) |

(52) U.S. Cl.
CPC .......... *A61B 5/02055* (2013.01); *A61B 5/00* (2013.01); *A61B 5/0402* (2013.01); *A61B 5/14542* (2013.01); *A61B 5/742* (2013.01); *A61B 5/7475* (2013.01); *G06F 19/3418* (2013.01); *G16H 10/20* (2018.01); *A61B 5/021* (2013.01); *A61B 5/024* (2013.01)

(58) Field of Classification Search
CPC ................................................. A61B 5/02055
USPC ........................................................ 600/301
See application file for complete search history.

(56) References Cited

U.S. PATENT DOCUMENTS

| | | |
|---|---|---|
| 5,262,944 A | 11/1993 | Weisner et al. |
| 5,447,164 A | 9/1995 | Shaya et al. |
| 5,473,536 A | 12/1995 | Wimmer |
| 5,647,369 A | 7/1997 | Petrucelli et al. |
| 5,715,451 A | 2/1998 | Marlin |
| 5,772,599 A | 6/1998 | Nevo et al. |
| 6,306,089 B1 | 10/2001 | Coleman et al. |
| 6,322,502 B1 | 11/2001 | Schoenberg et al. |
| 6,616,613 B1 | 9/2003 | Goodman |
| 6,773,397 B2 | 8/2004 | Kelly |
| 6,876,947 B1 | 4/2005 | Darley et al. |
| 7,311,666 B2 | 12/2007 | Stupp et al. |
| 7,338,453 B2 | 3/2008 | Warring-Davies |
| 7,374,535 B2 | 5/2008 | Schoenberg et al. |
| 2002/0177758 A1* | 11/2002 | Schoenberg .......... G06F 19/327 600/300 |
| 2003/0120164 A1 | 6/2003 | Nielsen et al. |
| 2004/0122486 A1 | 6/2004 | Stahmann et al. |
| 2005/0165768 A1* | 7/2005 | Coulson ............ G06F 17/30569 |
| 2008/0066052 A1* | 3/2008 | Wolfram ................... G06F 8/30 717/109 |
| 2014/0058714 A1* | 2/2014 | Boyer ................... G06F 19/345 703/11 |
| 2016/0127514 A1* | 5/2016 | Maksumov ............. H04L 69/08 709/202 |

FOREIGN PATENT DOCUMENTS

JP          11033022 A      2/1999

OTHER PUBLICATIONS

Philips "IntelliVue MP90" overview; http://www.medical.philips.com/us/products/patient_monitoring/products/intellivue_mp90 (downloaded May 13, 2008), p. 1-6.

Philips "IntelliVue MP90"; Philips advertising brochure; 2006, p. 1-3.

* cited by examiner

*Primary Examiner* — Jerry Lin

(57) ABSTRACT

In a medical monitoring system, one or more biometric monitors collect data of a plurality of monitored biometric parameters. An expression evaluator evaluates a user-defined expression incorporating one or more of the monitored biometric parameters to generate data for a user-defined biometric parameter. A further processing component performs processing and display of data of at least one parameter selected from the monitored biometric parameters and the user-defined biometric parameter. The further processing component operates in the same way regardless of whether the at least one parameter is selected from the monitored biometric parameters or the user-defined biometric parameter.

11 Claims, 2 Drawing Sheets

PATIENT MONITOR WITH USER-DEFINED MONITORED PARAMETERS

CROSS REFERENCE TO RELATED APPLICATIONS

This is a continuation of prior application Ser. No. 12/094,213 filed May 19, 2008, which is a national filing of PCT application Serial No. PCT/IB2006/054016, filed Oct. 20, 2006, published as WO 2007/060559 A2 on May 31, 2007, which claims the benefit of U.S. provisional application Ser. No. 60/739,744 filed Nov. 23, 2005, which is incorporated herein by reference.

BACKGROUND

The following relates to the medical monitoring arts. It finds particular application in bedside patient monitoring in clinical settings such as hospitals, intensive care units (ICU), cardiac care units (CCU), and so forth, and will be described with particular reference thereto. However, it also finds more general application in medical monitoring generally, including fetal monitoring, neonatal monitoring, pediatric monitoring, surgical patient monitoring, outpatient monitoring, home monitoring, veterinary monitoring, monitoring during aerobic workouts, and so forth.

Medical monitoring systems provide extensive information about the patient. In some systems, rack-mounted modular monitoring units can be selectively assembled to monitor selected medical parameters such as temperature, electrocardiographic (ECG) data, heart rate, oxygen saturation ($SpO_2$), breathing rate, blood pressure parameters, and so forth. The mounted modular monitoring units feed data into a monitoring system that plots or trends selected data, stores data for later review, or so forth.

Each monitored parameter typically includes a connection with the patient. For example, ECG monitoring includes four or more electrical contacts to the patient's skin, typically in the torso region near the heart. In some cases, a single connection to the patient may provide more than one monitored signal. For example, a single finger-clip monitor may provide both heart rate and $SpO_2$ data. To reduce the number of patient connections, some medical monitoring systems include derived parameters. For example, various blood pressure parameters such as arterial blood pressure, central venous pressure, and so forth, can be derived from a continuous blood pressure monitor. This facilitates increasing the number of monitored parameters without concomitant increase in the number of modular monitoring units and without concomitant increase in the number of patient probes.

The monitoring system typically also provides event monitoring, in which an alarm is sounded if and when a parameter exceeds a threshold. For example, an alarm may sound if and when the heart rate decreases below a lower threshold value, or exceeds an upper threshold value. Similarly, an alarm may sound if the oxygen saturation drops below a threshold such as 90%. Such event monitoring advantageously provides an efficient and immediate way to alert medical personnel to potentially life-threatening patient conditions.

Existing monitoring systems provide monitoring flexibility through the use of modular monitoring units and derived parameters. However, medical personnel are limited to those monitoring units and derived parameters provided by the monitoring system. Medical personnel often perform calculations and estimations using existing monitoring data to provide desired additional information.

Shaya et al., U.S. Pat. No. 5,447,164, discloses a medical monitoring system in which the user can set up user-defined events for alarming. This can enable medical personnel to better configure the medical monitoring system to alarm upon occurrence of potentially life-threatening patient conditions. For example, rather than alarming exclusively by thresholding the heart rate, an alarm can be triggered based on a user-selectable combination of heart rate and blood pressure thresholds. However, this approach does not provide medical personnel with additional information except upon occurrence of the selected alarm threshold.

BRIEF SUMMARY

According to one aspect, a medical monitoring system is disclosed. One or more biometric monitors are configured to collect samples of a plurality of monitored biometric parameters. An expression evaluator is configured to evaluate a user-defined expression incorporating one or more of the monitored biometric parameters to generate samples of a user-defined biometric parameter. A further processing component is configured to perform processing of samples of at least one parameter selected from the monitored biometric parameters and the user-defined biometric parameter. The further processing component operates in the same way regardless of whether the at least one parameter is selected from the monitored biometric parameters or the user-defined biometric parameter.

According to another aspect, a medical monitoring system is disclosed. One or more biometric monitors are configured to collect data of a plurality of monitored biometric parameters. An expression evaluator is configured to evaluate a user-defined expression incorporating one or more of the monitored biometric parameters to generate data for a user-defined biometric parameter. A further processing component is configured to perform processing of data of at least one parameter selected from the monitored biometric parameters and the user-defined biometric parameter. The further processing component operates in the same way regardless of whether the at least one parameter is selected from the monitored biometric parameters or the user-defined biometric parameter.

According to another aspect, a medical monitoring method is disclosed. Samples are collected of a plurality of monitored biometric parameters. A user-defined expression incorporating one or more of the monitored biometric parameters is evaluated to generate samples of a user-defined biometric parameter. Samples of at least one of the monitored biometric parameters and the user-defined biometric parameter are processed. The processing is performed in the same way for both the at least one monitored biometric parameter and for the user-defined biometric parameter.

According to another aspect, a computer device is programmed to perform a method including: (i) evaluating a user-defined expression incorporating one or more monitored biometric parameters to generate samples of a user-defined biometric parameter, (ii) processing samples of at least one of the monitored biometric parameters, and (iii) processing the user-defined biometric parameter. The processing operations are performed in the same way both for the samples of the at least one monitored biometric parameter and for the samples of the user-defined biometric parameter.

One advantage resides in improved patient monitoring flexibility.

Another advantage resides in improved appropriateness of biometric parameters selected for monitoring.

Another advantage resides enhancing information provided to medical personnel about a patient's medical condition.

Another advantage resides in providing enhanced information at the patients' bedside as well as throughout the monitoring system.

Numerous additional advantages and benefits will become apparent to those of ordinary skill in the art upon reading the following detailed description of the preferred embodiments.

BRIEF DESCRIPTION OF THE DRAWINGS

The invention may take form in various components and arrangements of components, and in various process operations and arrangements of process operations. The drawings are only for the purpose of illustrating preferred embodiments and are not to be construed as limiting the invention.

DETAILED DESCRIPTION OF THE PREFERRED EMBODIMENTS

Figure 1:
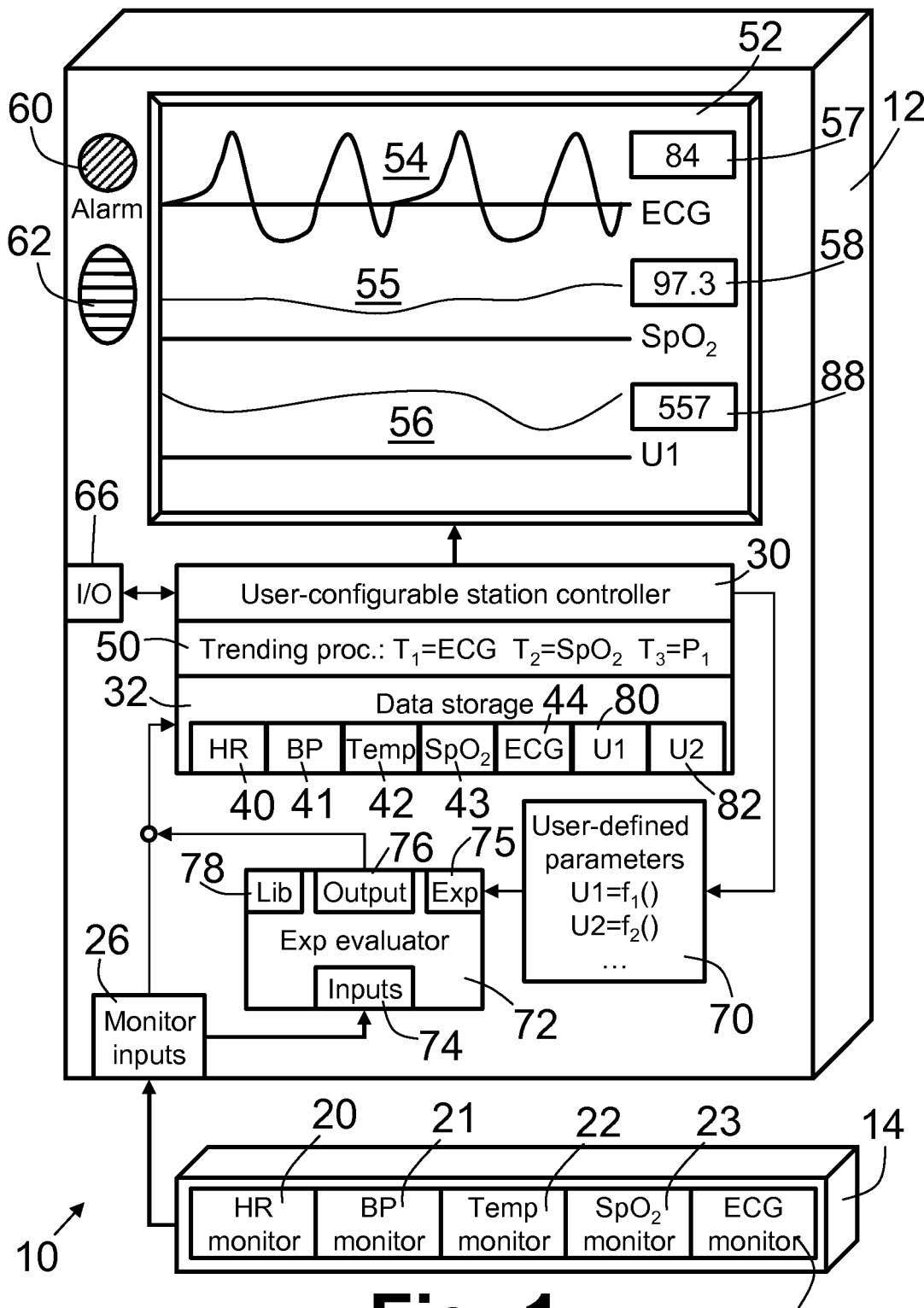
FIG. 1 diagrammatically shows a medical monitoring system.

With reference to FIG. 1, a medical monitoring system 10 includes a monitoring station 12 operatively connected with a modular biometric monitor rack 14. The rack 14 includes an example heart rate (HR) monitor module 20 configured to monitor patient heart rate, an example blood pressure monitor module 21 configured to monitor patient blood pressure, an example temperature monitor module 22 configured to monitor patient temperature, an example blood oxygen saturation ($SpO_2$) monitor module 23 configured to monitor patient blood oxygen saturation level, and an example electrocardiographic (ECG) monitor module 24 configured to monitor patient cardiac cycling. Additional, fewer, or other biometric parameters can be monitored. In some embodiments, a single monitor, which may or not be modular, is configured to monitor more than one biometric parameter.

Each of the biometric monitors 20, 21, 22, 23, 24 collects samples that are communicated to a monitoring inputs portion 26 of the monitoring station 12 as analog or digital signals. The samples are time-stamped, either by the biometric monitors 20, 21, 22, 23, 24 or by data pre-processing provided by the inputs portion 26 of the monitoring station 12. For example, some biometric monitors may include analog-to-digital capability so as to digitally communicate the biometric data as digital biometric parameter samples with associated digital time-stamps. Some biometric monitors may output continuous analog biometric data, and the data pre-processing of the monitoring inputs portion 26 of the monitoring station 12 suitably performs analog-to-digital conversion at a selected digitizing rate to generate time-stamped samples. While in the monitoring system 10 of FIG. 1 the biometric monitors 20, 21, 22, 23, 24 are physically separate from the monitoring station 12, in other embodiments one, some, or all of the biometric monitors may be integral with the monitoring station. Moreover, physically separate biometric monitors can be used in configurations other than the illustrated rack-mounted configuration.

A user-configurable station controller 30 controls operation of the monitoring station 12, including controlling operation of further processing components that are configured to perform processing of time-stamped biometric parameter samples. For example, the station controller 30 controls a data storage 32 that stores collected time-stamped samples of each biometric parameter using a common data storage format. The data storage 32 includes: a bin, data partition, file, or other storage structure 40 for storing time-stamped heart rate samples; a storage structure 41 for storing time-stamped blood pressure samples; a storage structure 42 for storing time-stamped patient temperature samples; a storage structure 43 for storing time-stamped blood oxygen saturation ($SpO_2$) samples; and a storage structure 44 for storing time-stamped electrocardiographic samples. Again, other physiological data or combinations of data can be stored. Further, all data may be encoded as to type of data and stored in a common data storage area.

A trending processor 50 also controlled by the station controller 30 performs real-time trending of selected parameters and displays this stored data via a graphical display 52. The illustrated display 52 includes three display regions 54, 55, 56 for displaying real-time waveform data and/or trend data of selected biometric parameters; however, other numbers of waveform and trending display regions may also be provided. In the illustrated example, the selected biometric parameters include electrocardiography (ECG) and blood oxygen saturation ($SpO_2$): the display region 54 is showing the real-time electrocardiographic data, while the display region 55 is trending blood oxygen saturation ($SpO_2$) data respective to time. The trending can be performed in real-time, for example by plotting samples acquired in the last five minutes respective to time, and scrolling older data off the left-side of the display 52 as time progresses and the display region becomes full. Alternatively or additionally, the trending can be retrospective, by plotting time-stamped samples recalled from the data storage 32 respective to time.

Other processing can be performed under the control of the station controller 30. For example, the display 50 is configured to display a real-time heart rate value (HR) in numeric area 57 and a real-time blood oxygen saturation value ($SpO_2$) in a numeric area 58. It is to be appreciated that the term "real-time" as used herein may denote a most-recently acquired time-stamped sample which is not necessarily the value at the present instant. For example, if a new $SpO_2$ sample is acquired every two seconds, then the real-time value shown in the numeric area 58 may have been acquired up to two seconds prior to the present instant.

Optionally, the monitoring station 12 includes an alarm, such as a visual alarm light 60, an audio alarm speaker 62, or so forth. If one or more of the trended parameters exceeds a threshold (such as a trended heart rate going below a lower threshold, or a trended blood pressure going above an upper threshold), then the alarm 60, 62 suitably activates to warn medical personnel of a potential problem with specific alarm information being displayed on display 52.

To enable user interfacing and the exchange of data, in addition to the display 50 the monitoring station 12 also includes an input/output (I/O) portion 66. In some embodiments, the I/O portion 66 enables the monitoring station 12 to be interfaced with a computer (not shown in FIG. 1), and the user can input configuration parameters or so forth via the computer and the I/O portion 66. In another embodiment, the I/O portion 66 enables the monitoring station 12 to be interfaced with a network such as a hospital local area network (HLAN) and to be able to receive additional time-stamped clinical information (blood gas data, lab results, etc., not shown in FIG. 1), which the user can utilize as additional input configuration parameters or so forth via the HLAN and the I/O portion 66. Alternatively, the monitoring station 12 optionally incorporates a keypad, keyboard, touch-sensitive screen, or other user input device (not shown) to enable user input. It is also contemplated to include in the I/O portion 66 the capability of exporting time-stamped biometric parameter samples stored in the data storage 32. For example, the 110 portion 66 optionally includes a USB port, Ethernet connection, or other interface for transferring time-stamped biometric parameter samples or other data to or from a connected computer or any other device on the HLAN.

The modular biometric monitors rack 14 enables the monitoring system 10 to monitor a variety of monitored biometric parameters, such as the example illustrated heart rate, blood pressure, patient temperature, blood oxygen saturation, and electrocardiographic data. However, medical personnel may want to have real-time and/or continuous monitoring of biometric parameters other than monitored biometric parameters provided by the installed biometric monitors 20, 21, 22, 23, 24.

Accordingly, the user can construct one or more user-defined biometric parameters that are stored in a user-defined biometric parameters storage 70. Each user-defined biometric parameter is defined by a user-defined expression incorporating one or more of the monitored biometric parameters, or one or more of the clinical biometric parameters received via the HLAN to generate time-stamped samples of the user-defined biometric parameter. An expression evaluator 72 receives the time-stamped monitored biometric parameters as inputs 74, and evaluates the user-defined expression 75 to generate as output 76 time-stamped samples of the user-defined biometric parameter. Optionally, the expression evaluator 72 includes or has access to a library 78 of pre-defined functions. The library 78 may include general mathematical, statistical, or calculus functions such as logarithm, integral "Int( )", or average "Avg( )". The library 78 may additionally or alternatively include pre-defined biometric parameters such as systolic arterial blood pressure (ABPsys) or diastolic arterial blood pressure (ABPdia). Optionally, the user-defined expression further incorporates one or more patient-specific inputs. For example, the user-defined expression may incorporate patient weight, patient age, patient gender, patient disease type, patient disease severity, or so forth. These patient-specific inputs may be entered manually, or may be read from an electronic patient database stored on a server of the HLAN or on another digital device connected with the monitoring station 12.

The generated time-stamped samples of the user-defined biometric parameter are subsequently treated by further processing components in the same way as the monitored biometric parameters, and can be similarly stored, trended, displayed in real-time, or so forth. For example, as representatively illustrated in FIG. 1, two user-defined biometric parameters denoted "U1" and "U2" are stored in the data storage 32 in the same way as the monitored biometric parameters are stored and in the same way as the user selected clinical biometric parameters received via the HLAN. A storage structure 80 is provided for storing the user-defined biometric parameter "U1" and a storage structure 82 is provided for storing the user-defined biometric parameter "U2". The data storage 32 operates in the same way for both the monitored biometric parameters (stored in storage structures 40, 41, 42, 43, 44) and the user-defined biometric parameters (stored in storage structures 80, 82).

The user-defined biometric parameters and user selected clinical biometric parameters received via the HLAN can also be trended in the same way as the monitored biometric parameters. As representatively illustrated in FIG. 1, the user-defined biometric parameter "U1" is displayed as a real-time waveform in the third display region 56 in the same way that the monitored electrocardiographic (ECG) is displayed or is displayed as trend data in the same way that the blood oxygen saturation ($SpO_2$) biometric parameters are trended in the display regions 54, 55, respectively. Such trending of the user-defined biometric parameters can be done in real-time or retrospectively, the latter using data stored in the data storage 32. Additionally, the display 50 is configured to display a real-time value of the user-defined biometric parameter "U1" in a numeric area 88 in the same way the display 50 is configured to display a real-time value of the blood oxygen saturation ($SpO_2$) in the numeric area 58. Optionally, the alarm 60, 62 can be configured to activate if the trended user-defined biometric parameter "U1" exceeds a selected threshold value. In a similar fashion, time-stamped samples of the user-defined biometric parameters can be exported from the data storage 32 via the I/O portion 66 of the monitoring station 12.

In summary, the expression evaluator 72 outputs time-stamped samples of the user-defined biometric parameters having the same format as the time-stamped user selected clinical biometric parameters received via the HLAN and as the time-stamped samples of the monitored biometric parameters output by the monitoring inputs portion 26 of the monitoring station 12. The time-stamped samples of the user-defined biometric parameters are stored in the data storage 32 using the same data storage format as for storing the user selected clinical biometric parameters received via the HLAN and as for storing the time-stamped samples of the monitored biometric parameters. Accordingly, the further processing components 32, 50, 52, 58, 88, 60, 62, 66 can process either monitored biometric parameters, user selected clinical biometric parameters received via the HLAN, or user-defined biometric parameters in the same way. These further processing components 32, 50, 52, 58, 88, 60, 62, 66 perform processing of time-stamped samples biometric parameters by operating in the same way regardless of whether the biometric parameter or parameters undergoing processing are selected from the monitored biometric parameters, the user selected clinical biometric parameters received via the HLAN, or the user-defined biometric parameter.

Figure 2:
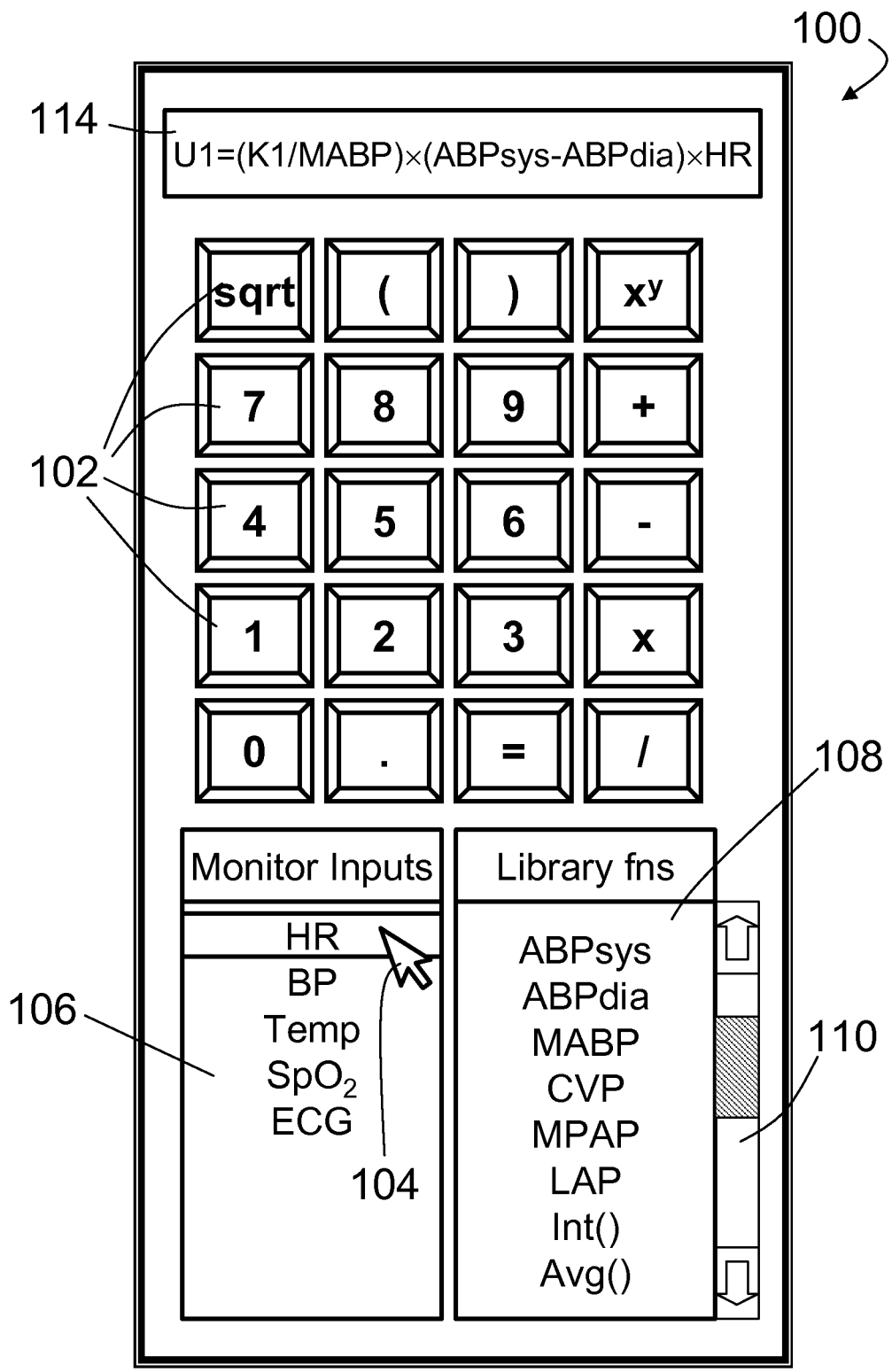
FIG. 2 diagrammatically shows a user interface for user input of a user-defined expression corresponding to a user-defined biometric parameter.

With reference to FIG. 2, a suitable user interface 100 for user input of a user-defined expression corresponding to a user-defined biometric parameter is shown. In some embodiments, the user interface 100 is displayed on the display 50, which in these embodiments is a touch-sensitive display enabling a user to operate user interface controls. Typical controls include keys 102 or a pointer 104 used to select from a list 106 of the monitored biometric parameters and of the user selected clinical biometric parameters received via the HLAN, or used to select from a list 108 of the functions stored in the library 78 (including operating a scroll-bar 110 to access listed functions that do not fit in the window of the list 108), or optionally usable to operate the keys 102. In some embodiments, the user interface 100 is displayed on a computer (not shown) connected with the monitoring station 12 by the I/O portion 66, and the controls 102, 104, 106, 108, 110 are suitably operated using a keyboard, mouse, touch-sensitive screen, or other input of the connected computer. In some embodiments, the user interface 100 is displayed on the display 50, which in these embodiments may or may not be touch-sensitive, and the monitoring station 12 includes a keyboard, trackball, or other input device (not shown) by which the user operates the controls 102, 104, 106, 108, 110. The user interface 100 also includes a display region 114 in which the user-entered expression is displayed.

In the representative illustration of FIG. 2, the user inputted expression is:

$$U1=(K1/MABP)\times(ABPsys-ABPdia)\times HR \quad (1),$$

where "HR" represents the heart rate monitored biometric parameter selected from the monitored biometric parameters list 106, "K1" can be a constant factor that is a function of age or disease state, "MABP" represents the mean arterial blood pressure library function selected from the library functions list 108, "ABPsys" represents the systolic arterial blood pressure library function selected from the library functions list 108, "ABPdia" represents the diastolic arterial blood pressure library function selected from the library functions list 108, and "U1" represents the user-defined biometric parameter whose expression is being input or edited. The expression of Equation (1) provides an estimate of cardiac output, a parameter whose measurement typically includes the surgical implantation of a measuring device into the arteries. The user may alternatively denote the user-defined biometric parameter, "U1", with an actual name of what they are calculating. For example, "U1" of equation (1) could be labeled "CO" for cardiac output or "$CO_c$" for calculated cardiac output or "$CO_u$" for user defined cardiac output. This can be a useful user-defined, non-invasively measured biometric parameter for diagnosing or monitoring certain cardiac conditions.

Another suitable candidate for implementation as user-defined biometric parameters is the pulmonary and systemic afterload opposing ventricular emptying of the right and left ventricles, respectively. Although afterload is a combination of several forces that oppose ventricular emptying, most of the component forces of afterload are not readily or reliably measured by bedside biometric monitors. However, as a major component of afterload is the resistance to ventricular outflow, the systemic vascular resistance (SVR) or pulmonary vascular resistance (PVR) are suitably estimated by:

$$U2=(MABP-CVP)/((K1/MABP)\times(ABPsys-ABPdia)\times HR) \quad (2),$$

$$U3=(MPAP-LAP)/((K1/MABP)\times(ABPsys-ABPdia)\times HR) \quad (3),$$

where "MABP" represents the mean arterial blood pressure library function selected from the library functions list 108, "CVP" represents the central venous pressure library function selected from the library functions list 108, "MPAP" represents the mean pulmonary artery pressure library function selected from the library functions list 108, and "LAP" represents the left-atrial pressure library function selected from the library functions list 108. Equation (2) assigns an estimate of the SVR to the user-defined biometric parameter "U2", while Equation (3) assigns an estimate of the PVR to the user-defined biometric parameter "U3".

While three user-defined biometric parameters "U1", "U2", and "U3" are used in the illustrated representative monitoring system 10, it will be appreciated that the number of user-defined biometric parameters can be one, two, three, four, or more. In some embodiments in which multiple user-defined biometric parameters are provided, the value of one user-defined biometric parameter may be incorporated into one of the other user-defined biometric parameters. For example, if the user-defined biometric parameter "U1" is defined by the expression of Equation (1), then the expression of Equation (3) can be written as:

$$U3=(MPAP-LAP)/U1 \quad (4).$$

The expression input via the user interface 100 can be stored in the user-defined biometric parameters storage 70 and processed by the expression evaluator 72 in various ways. For example, in some embodiments, the expression defining the user-defined biometric parameter is stored in a textual form, optionally parsed, in the user-defined biometric parameters storage 70. The expression evaluator 72 then includes processing for converting the textual expression into a compiled or otherwise processed expression suitable for numeric evaluation to generate time-stamped samples of the user-defined biometric parameter. In other embodiments, the expression can be stored in the user-defined biometric parameters storage 70 in the compiled or otherwise processed format, which typically speeds computation of user-defined biometric parameters by the expression evaluator 72.

The time-stamped samples acquired for the monitored biometric parameters may or may not be in synch. In other words, the time-stamped samples acquired for the monitored biometric parameters may or may not have the same time-stamp. In some embodiments, for example, the monitor inputs portion 26 may acquire samples of each monitored biometric parameter at about the same time, and repeat this acquisition at fixed time intervals such as every two seconds. In this case, the expression evaluator 72 is suitably applied every two seconds to generate user-defined biometric parameter samples with the same time-stamp as the monitored biometric parameters, incremented every two seconds. In such an arrangement, the samples are optionally made time-identifiable in the data storage 32 by including a single common time-stamp value for each set of substantially simultaneously acquired samples, such as in the following example comma-delimited text format:

13:00:00, S(HR), S(BP), S(Temp), S($SpO_2$), S(ECG), S(U1), S(U2)
13:00:02, S(HR), S(BP), S(Temp), S($SpO_2$), S(ECG), S(U1), S(U2)
13:00:04, S(HR), S(BP), S(Temp), S($SpO_2$), S(ECG), S(U1), S(U2)
. . .

where each comma-delimited line stores comma-delimited samples having about the same time-stamp, the first value of each line is the time-stamp (shown in this example in the form "HH:MM:SS" where "HH" denotes hours, "MM" denote minutes, and "SS" denotes seconds), and the notation "S( )" denotes a numeric sample value for the biometric parameter indicated within the parentheses (for example, "S(HR)" denotes a specific numeric sample value of the heart rate biometric parameter). If the time increment for the samples is constant, then the samples can be made time-identifiable by storing the start time of acquisition, such as:

Time start=13:00:00 Time increment=00:00:02
S(HR), S(BP), S(Temp), S($SpO_2$), S(ECG), S(U1), S(U2)
S(HR), S(BP), S(Temp), S($SpO_2$), S(ECG), S(U1), S(U2)
S(HR), S(BP), S(Temp), S($SpO_2$), S(ECG), S(U1), S(U2)
. . .

On the other hand, in some embodiments the various monitored biometric parameter samples may be acquired at different times, so that each monitored biometric parameter should be stored in the data storage 32 with its own time-stamp. In these embodiments, the expression evaluator 72 suitably computes each time-stamped user-defined biometric parameter sample using those monitored biometric parameter samples or user selected clinical biometric parameters received via the HLAN that have time-stamps closest to or utilizes the last valid timed-stamped sample until a new valid entry is received of the user-defined biometric parameter value. Alternatively, interpolation can be used to generate monitored biometric parameter sample values at the time-stamp of the user-defined biometric parameter sample being generated.

Instead of storing the time-stamped biometric parameter sample values in text format, a suitable numeric storage format can be used, such as a floating point binary representation of the time-stamp and sample values. Regardless of the particular type of storage selected, the monitored biometric parameters and the user-defined biometric parameters are stored in the same way (e.g., all as text values, or all as floating-point binary values, or so forth) so that the further processing components 32, 50, 52, 58, 88, 60, 62, 66 can readily process both monitored biometric parameters and user-defined biometric parameters in the same way.

The illustrated monitoring system 10 is a general-purpose monitoring system suitable for use at patient bedside, in an intensive care unit (ICU), in a cardiac care unit (CCU), or so forth. However, the disclosed features are applicable in medical monitoring generally, and will find application in fetal monitoring, neonatal monitoring, pediatric monitoring, surgical patient monitoring, outpatient monitoring, home monitoring, veterinary monitoring, monitoring during aerobic workouts, and so forth. For example, the medical monitoring features disclosed herein are readily integrated into medical monitoring systems that are components of exercise equipment such as stationary bicycles, treadmills, or so forth, are readily integrated into medical monitoring systems that are integrated components of neonatal care units, or integrated onto home monitoring systems, or so forth.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A medical monitoring system comprising:
   one or more biometric monitors configured to collect time-stamped samples of a plurality of monitored biometric parameters;
   an expression evaluator comprising a computer configured to generate time-stamped samples of a user-defined biometric parameter defined by a user-defined expression by evaluating the user-defined expression for one or more of the monitored biometric parameters incorporated into the user-defined expression;
   a data storage including a first storage structure corresponding to each monitored biometric parameter configured to store the time-stamped samples of the corresponding monitored biometric parameter and a second storage structure corresponding to each user-defined biometric parameter configured to store the time-stamped samples of the corresponding user-defined biometric parameter;
   a graphical display including a plurality of display regions; and
   a station controller that is user-configurable to select a monitored biometric parameter or user-defined biometric parameter for each display region of the display component, the station controller configured to display in each display region a trend of time-stamped samples of the selected monitored biometric parameter or user-defined biometric parameter stored in the corresponding storage structure of the data storage by plotting the time-stamped samples of the selected monitored biometric parameter or user-defined biometric parameter respective to time as indicated by the time stamps of the time-stamped samples.

2. The medical monitoring system of claim 1, wherein:
   the data storage includes said first storage structure corresponding to each monitored biometric parameter configured to store the time-stamped samples of the corresponding monitored biometric parameter in a floating point binary format and said second storage structure corresponding to each user-defined biometric parameter configured to store the time-stamped samples of the corresponding user-defined biometric parameter in the same floating point binary format as the stored time-stamped samples of the monitored biometric parameters.

3. The medical monitoring system of claim 1, wherein:
   the data storage includes said first storage structure corresponding to each monitored biometric parameter configured to store the time-stamped samples of the corresponding monitored biometric parameter in a text value format and said second storage structure corresponding to each user-defined biometric parameter configured to store the time-stamped samples of the corresponding user-defined biometric parameter in the same text value format as the stored time-stamped samples of the monitored biometric parameters.

4. The medical monitoring system as set forth in claim 1, wherein the one or more biometric monitors are configured to collect time-stamped samples of a plurality of monitored biometric parameters including at least two monitored biometric parameters selected from the group consisting of: heart rate, blood pressure, temperature, blood oxygen saturation ($SpO_2$), and electrocardiographic (ECG) data.

5. The medical monitoring system of claim 1 wherein:
   the data storage is configured to store the time-stamped samples in each storage structure of the data storage in the same format including (1) the same time stamp format and (2) the same sample value representation format, regardless of whether the storage structure corresponds to a monitored biometric parameter or to a user-defined biometric parameter.

6. The medical monitoring system of claim 5, the time stamp format is a floating point binary time stamp format and the sample value representation format is a floating point binary sample value representation format.

7. The medical monitoring system of claim 5, the time stamp format is a text value time stamp format and the sample value representation format is a text value sample value representation format.

8. The medical monitoring system as set forth in claim 5, wherein the one or more biometric monitors are configured to collect time-stamped samples of a plurality of monitored biometric parameters including at least two monitored biometric parameters selected from the group consisting of: heart rate, blood pressure, temperature, blood oxygen saturation ($SpO_2$), and electrocardiographic (ECG) data.

9. A medical monitoring system comprising:
   one or more biometric monitors configured to collect time-stamped samples of a plurality of monitored biometric parameters including at least two monitored biometric parameters selected from the group consisting of: heart rate, blood pressure, temperature, blood oxygen saturation (SpO$_2$), and electrocardiographic (ECG) data;

a first data storage;

a second data storage; and an expression evaluator comprising a computer configured to:

generate time-stamped samples of a user-defined biometric parameter defined by a user-defined expression by evaluating the user-defined expression for the collected time-stamped samples of one or more of the monitored biometric parameters incorporated into the user-defined expression;

store the collected time-stamped samples of the plurality of monitored biometric parameters in the first data storage in a format including a time stamp format for time stamps of the time-stamped samples and a sample value representation format for the samples;

store the time-stamped samples of the user-defined biometric parameter in the second data storage in the same format as the collected time-stamped samples of the monitored biometric parameters, the same format including the same time stamp format and the same sample value representation format; and a display component configured to process and display a trend of time-stamped samples of at least one parameter selected from the monitored biometric parameters and the user-defined biometric parameter by plotting the time-stamped samples respective to time as indicated by the time stamps of the time-stamped samples.

10. The medical monitoring system of claim 9 wherein the time stamp format is a floating point binary time stamp format and the sample value representation format is a floating point binary sample value representation format.

11. The medical monitoring system of claim 9 wherein the time stamp format is a text value time stamp format and the sample value representation format is a text value sample value representation format.

\* \* \* \* \*